US010232473B2

(12) United States Patent
Zhou et al.

(10) Patent No.: US 10,232,473 B2
(45) Date of Patent: Mar. 19, 2019

(54) SYSTEM AND METHOD FOR PERFORMING LASER INDUCED BREAKDOWN SPECTROSCOPY DURING LASER ABLATION COATING REMOVAL

(71) Applicant: General Electric Company, Schenectady, NY (US)

(72) Inventors: Ying Zhou, Niskayuna, NY (US); Hongqiang Chen, Niskayuna, NY (US); Matthew Vaughan Schulmerich, Niskayuna, NY (US); Jason Christopher Gritti, West Chester, OH (US)

(73) Assignee: General Electric Company, Schenectady, NY (US)

( * ) Notice: Subject to any disclaimer, the term of this patent is extended or adjusted under 35 U.S.C. 154(b) by 279 days.

(21) Appl. No.: 15/055,291

(22) Filed: Feb. 26, 2016

(65) Prior Publication Data
US 2017/0247797 A1    Aug. 31, 2017

(51) Int. Cl.
*C23F 4/00* (2006.01)
*B23P 6/00* (2006.01)
(Continued)

(52) U.S. Cl.
CPC .............. *B23P 6/002* (2013.01); *B23K 26/36* (2013.01); *F01D 5/005* (2013.01); *G01N 21/718* (2013.01);
(Continued)

(58) Field of Classification Search
CPC ....... B23P 6/002; B23K 26/36; G01N 21/718; G01N 2021/8427; F01D 5/005; F05D 2230/13; F05D 2260/83
See application file for complete search history.

(56) References Cited

U.S. PATENT DOCUMENTS 5,446,538 A  *  8/1995  Noll ..................... G01N 21/718
                                                        356/318
5,571,416 A  *  11/1996  Halsup ................. B01D 21/267
                                                        137/177
(Continued)

OTHER PUBLICATIONS

Kanawande, R., et al., "Qualitative tissue differentiation by analysing the intensity ratios of atomic emission lines using laser induced breakdown spectroscopy (LIBS): Prospects for a feedback mechanism for surgical laser systems", Journal of Biophotonics, vol. 8, Issue 1-2, Jan. 1, 2015, pp. 153-161.

(Continued)

*Primary Examiner* — Nahida Sultana
(74) *Attorney, Agent, or Firm* — GE Global Patent Operation; Nitin N. Joshi

(57) ABSTRACT

A system and method for performing laser induced breakdown spectroscopy during laser ablation of a coating, such as a TBC coating, deposited on a surface of a component, particularly to enable obtained spectrometry signals of the ablated coating to be used to monitor and control the laser ablation removal process in real-time. The system includes a laser energy source and a scan head interconnected with the laser energy source to receive a laser beam therefrom and then direct the laser beam onto the surface of the coated component. Collection optics collect radiation emitted from a laser-induced plasma generated by the laser beam at the surface of the coated component. The system is further equipped to spectrally analyze the radiation and generate a feedback signal for control and optimization of one or more operational parameters of the laser energy source in real-time.

15 Claims, 6 Drawing Sheets

(51) Int. Cl.
- *B23K 26/36* (2014.01)
- *F01D 5/00* (2006.01)
- *G01N 21/71* (2006.01)
- *G01N 21/84* (2006.01)

(52) U.S. Cl.
CPC ...... *F05D 2230/13* (2013.01); *F05D 2260/83* (2013.01); *G01N 2021/8427* (2013.01)

(56) References Cited

U.S. PATENT DOCUMENTS

| | | | | |
|---|---|---|---|---|
| 5,847,825 | A * | 12/1998 | Alexander | G01N 21/718 356/318 |
| 6,008,896 | A * | 12/1999 | Sabsabi | G01N 21/718 356/318 |
| 6,762,835 | B2 * | 7/2004 | Zhang | G01J 3/443 356/318 |
| 6,762,836 | B2 | 7/2004 | Benicewicz et al. | |
| 7,016,035 | B2 | 3/2006 | Wu et al. | |
| 7,064,825 | B2 | 6/2006 | Viertl et al. | |
| 7,251,022 | B2 * | 7/2007 | Martin | G01J 3/36 356/318 |
| 7,271,898 | B2 * | 9/2007 | Weber | G01N 21/718 356/317 |
| 7,440,097 | B2 * | 10/2008 | Benicewicz | G01J 3/2889 356/316 |
| 7,535,565 | B1 | 5/2009 | Viertl et al. | |
| 8,440,933 | B2 * | 5/2013 | Marcus | B23K 26/032 219/121.62 |
| 9,116,126 | B2 | 8/2015 | Hassan et al. | |
| 9,506,869 | B2 * | 11/2016 | Quant | G01N 21/718 |
| 2004/0102764 | A1 * | 5/2004 | Balling | A61F 9/008 606/5 |
| 2005/0068524 | A1 * | 3/2005 | Wu | G01J 3/02 356/316 |
| 2007/0265783 | A1 * | 11/2007 | Mound | G01J 3/02 702/8 |
| 2015/0076125 | A1 * | 3/2015 | Toyosawa | B01J 19/12 219/121.79 |
| 2018/0021886 | A1 * | 1/2018 | Ushiroda | B23K 26/046 219/121.78 |
| 2018/0275068 | A1 * | 9/2018 | Ozcan | G01N 1/34 |

OTHER PUBLICATIONS

Tong, T., Li, J., and Longlin, J.P., "Ultrafast Laser-Induced Breakdown Spectroscopy and Application to Real-Time Control of Ultrafast Laser Micromachining Process", J. Turbomach. ASME Summer Heat Transfer Conference (2003), pp. 1-9.

Tong, T., Li, J., and Longlin, J.P., "Real-time control of ultrafast laser micromachining by laser-induced breakdown spectroscopy", Applied Optics, vol. 43, No. 9 (2004), pp. 1971-1980.

* cited by examiner

SYSTEM AND METHOD FOR PERFORMING LASER INDUCED BREAKDOWN SPECTROSCOPY DURING LASER ABLATION COATING REMOVAL

BACKGROUND

The present disclosure generally relates to systems and methods for coating removal. More particularly, this disclosure is directed to a system and method that provides real-time compositional feedback to a laser ablation machine in order to identify when the ablation process has reached an optimal end point during a coating removal process.

Hot section components of turbomachines, including gas turbines employed for power generation and propulsion, are often protected by one or more coating layers, such as a thermal barrier coating (TBC), to reduce the temperature of the underlying component substrate and thereby prolong the service life of the component. Ceramic materials and particularly yttria-stabilized zirconia (YSZ) are widely used as TBC materials because of their high temperature capability, low thermal conductivity, and relative ease of deposition by plasma spraying, flame spraying and physical vapor deposition (PVD) techniques. Plasma spraying processes such as air plasma spraying (APS) yield noncolumnar coatings characterized by a degree of inhomogeneity and porosity, and have the advantages of relatively low equipment costs and ease of application. TBC's employed in the highest temperature regions of turbomachines are often deposited by PVD, particularly electron-beam PVD (EBPVD), which yields a strain-tolerant columnar grain structure. Similar columnar microstructures with a degree of porosity can be produced using other atomic and molecular vapor processes.

To be effective, a TBC must strongly adhere to the component and remain adherent throughout many heating and cooling cycles. The latter requirement is particularly demanding due to the different coefficients of thermal expansion (CTE) between ceramic materials and the substrates they protect, which are typically superalloys, though ceramic matrix composite (CMC) materials are also used. An oxidation-resistant bond coat is often employed to promote adhesion and extend the service life of a TBC, as well as protect the underlying substrate from damage by oxidation and hot corrosion attack. Bond coats used on superalloy substrates are typically in the form of a diffusion aluminide coating or an overlay coating such as MCrAlX (where M is iron, cobalt and/or nickel, and X is yttrium, a rare earth element, or a reactive element). During the deposition of the ceramic TBC and subsequent exposures to high temperatures, such as during turbine operation, these bond coats form a tightly adherent alumina ($Al_2O_3$) layer or scale that adheres the TBC to the bond coat.

During the manufacture and/or maintenance of the turbine component and deposition of a one or more layers of a protective coating material thereon, portions of the component intended to be free of any coating material may become at least partially covered during the coating process. In addition, the service life of these one or more protective coating layers is typically limited by a spallation event driven by bond coat oxidation, increased interfacial stresses, and the resulting thermal fatigue. In either situation, removal of the protective coating layer is required.

In current manufacturing processes laser ablation may be utilized for coating removal by rapidly scanning a laser beam across a coated surface with multiple passes to remove a desired material thickness (such as TBC coating removal on the LEAP S1B trailing edge cooling slot). However, the number of passes that are required to completely remove a desired layer, while not breaking into the sub layers, is determined empirically by trial and error or with a gage to measure the physical material removed (depth or mass). For applications such as TBC coating removal on LEAP S1B trailing edge cooling slots, tight tolerances necessitate optimized laser ablation to avoid tedious manual inspection and then rework which is time consuming and incurs high manufacturing cost.

Typical laser ablation coating removal processes employ a laser pulse to remove materials. Laser induced breakdown spectroscopy (LIBS), as an analytical method, employs the same laser pulse. As known in the art, LIBS entails projecting a pulsed laser beam onto a material at a power density sufficient to vaporize (ablate) a small portion of the material and generate a luminous plasma that contains the characteristic atomic emission lines of elements within the material, which are then collected for spectral analysis. LIBS systems employ the use of real-time measurements to enable this spectral analysis, facilitating real-time monitoring and control.

Accordingly there is an ongoing need for more convenient and less obtrusive techniques to remove coating materials. It would be desirable to provide a robust removal process that is operational regardless of coating thickness variation, avoids sublayer damage, and minimizes tedious manual inspection of reworked-parts. It would also be desirable to provide a system and method that integrates real-time measurement with an existing laser removal process thus enabling real-time monitoring and control.

BRIEF DESCRIPTION

In accordance with one exemplary embodiment, disclosed is a system for performing laser induced breakdown spectroscopy during a laser ablation coating removal process. The system includes a laser energy source, a scan head, one or more collection optics, means for spectrally analyzing the radiation collected by the collection optics and a control unit. The laser energy source is configured to perform the laser induced breakdown spectroscopy and laser ablation coating removal process. The scan head is interconnected with the laser energy source to receive a laser beam emitted therefrom. The scan head is positioned sufficiently close to an article to enable the laser beam exiting the laser energy source to be directed onto a surface of the article defined by a coating to ablate at least a portion of the coating. The one or more collection optics collect radiation emitted from a laser-induced plasma generated by the laser beam at the surface of the coating. The means for spectrally analyzing the radiation collected by the collection optics generates a signal representative of the chemical composition of the collected radiation. The control unit receives the signal from the means for spectrally analyzing the radiation and generates a feedback signal for control and optimization of one or more operational parameters of the laser energy source in real-time.

In accordance with another exemplary embodiment, disclosed is a system for laser induced breakdown spectroscopy of a three-dimensional surface of a turbine component of a turbomachine during a laser ablation coating removal process. The system includes a laser energy source, a scan head, one or more collection optics, a spectrometer, and a control unit. The laser energy source is configured to perform the laser induced breakdown spectroscopy and the laser ablation coating removal process. The scan head is interconnected with the laser energy source to receive a laser beam emitted therefrom. The scan head is positioned sufficiently close to the turbine component to enable the laser beam exiting the laser energy source to be directed onto the three-dimensional surface of the turbine component defined by a coating, to ablate at least a portion of the coating. The one or more collection optics collect radiation emitted from a laser-induced plasma generated by the laser beam at the three-dimensional surface of the turbine component. The spectrometer spectrally analyzes the radiation collected by the collection optics and generates a signal representative of the chemical composition of the collected radiation. The control unit receives the signal from the spectrometer and generates a feedback signal for control and optimization of one or more operational parameters of the laser energy source in real-time.

In accordance with yet another exemplary embodiment, disclosed is a method of performing laser induced breakdown spectroscopy on a three-dimensional surface of a component. The method includes generating a laser beam with a laser energy source that is configured to perform the laser induced breakdown spectroscopy and the laser ablation coating removal process. The method further including transmitting the laser beam to the three-dimensional surface of the component to ablate at least a portion of a coating disposed on the three-dimensional surface of the component, collecting radiation emitted from a laser-induced plasma generated by the laser beam during ablation of at least a portion of the coating and spectrally analyzing the radiation emitted from the laser-induced plasma to detect and measure one or more specific transient species within the laser-induced plasma and generate a signal representative of a chemical composition of the collected radiation. A feedback signal is next generated in response to the signal representative of the chemical composition of the collected radiation, for control and optimization of one or more operational parameters of the laser energy source in real-time.

Other objects and advantages of the present disclosure will become apparent upon reading the following detailed description and the appended claims with reference to the accompanying drawings. These and other features and improvements of the present application will become apparent to one of ordinary skill in the art upon review of the following detailed description when taken in conjunction with the several drawings and the appended claims.

DRAWINGS

The above and other features, aspects, and advantages of the present disclosure will become better understood when the following detailed description is read with reference to the accompanying drawings in which like characters represent like parts throughout the drawings, wherein.

Figure 4:
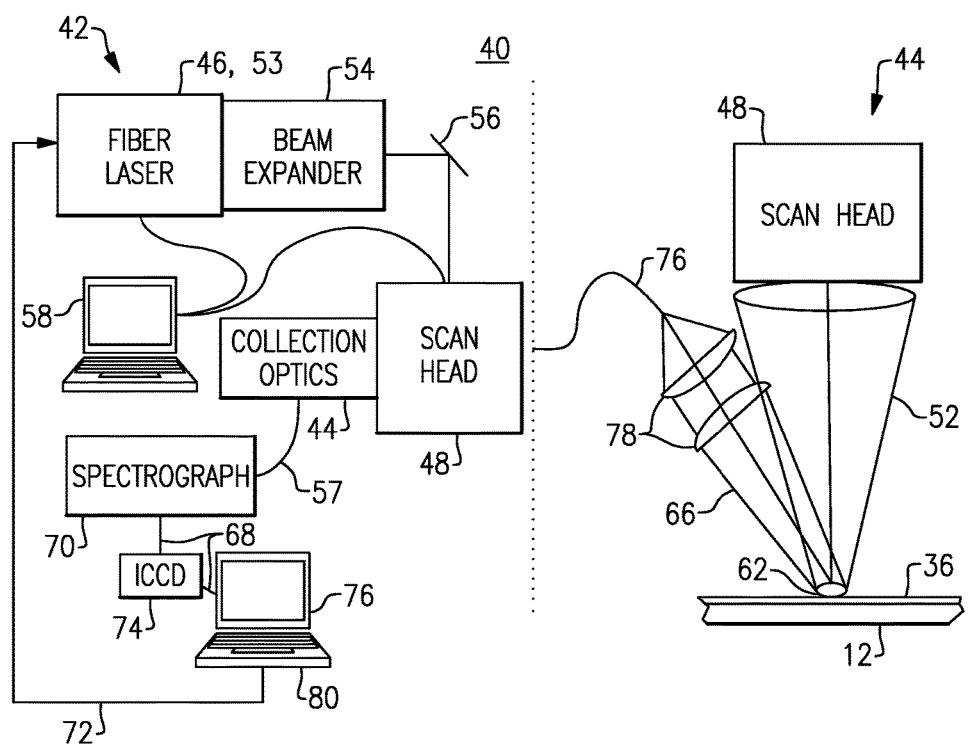
Figure 5:
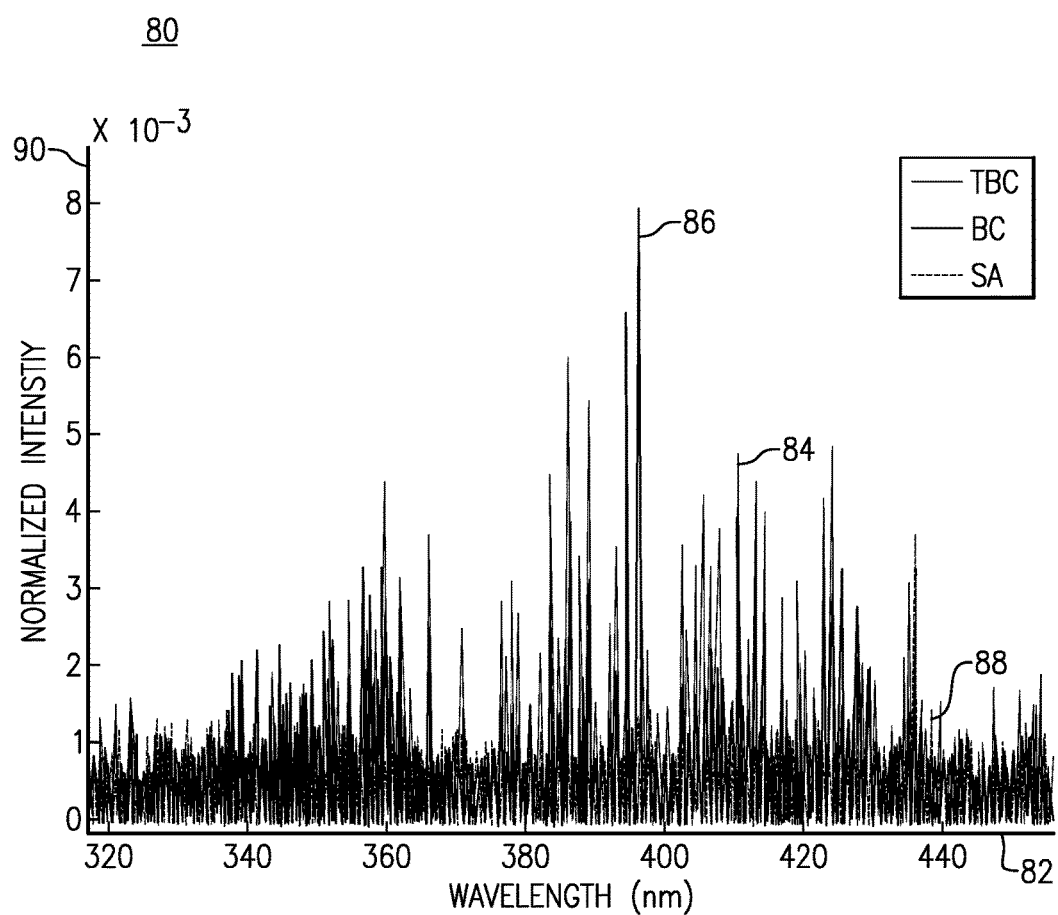
Figure 6:
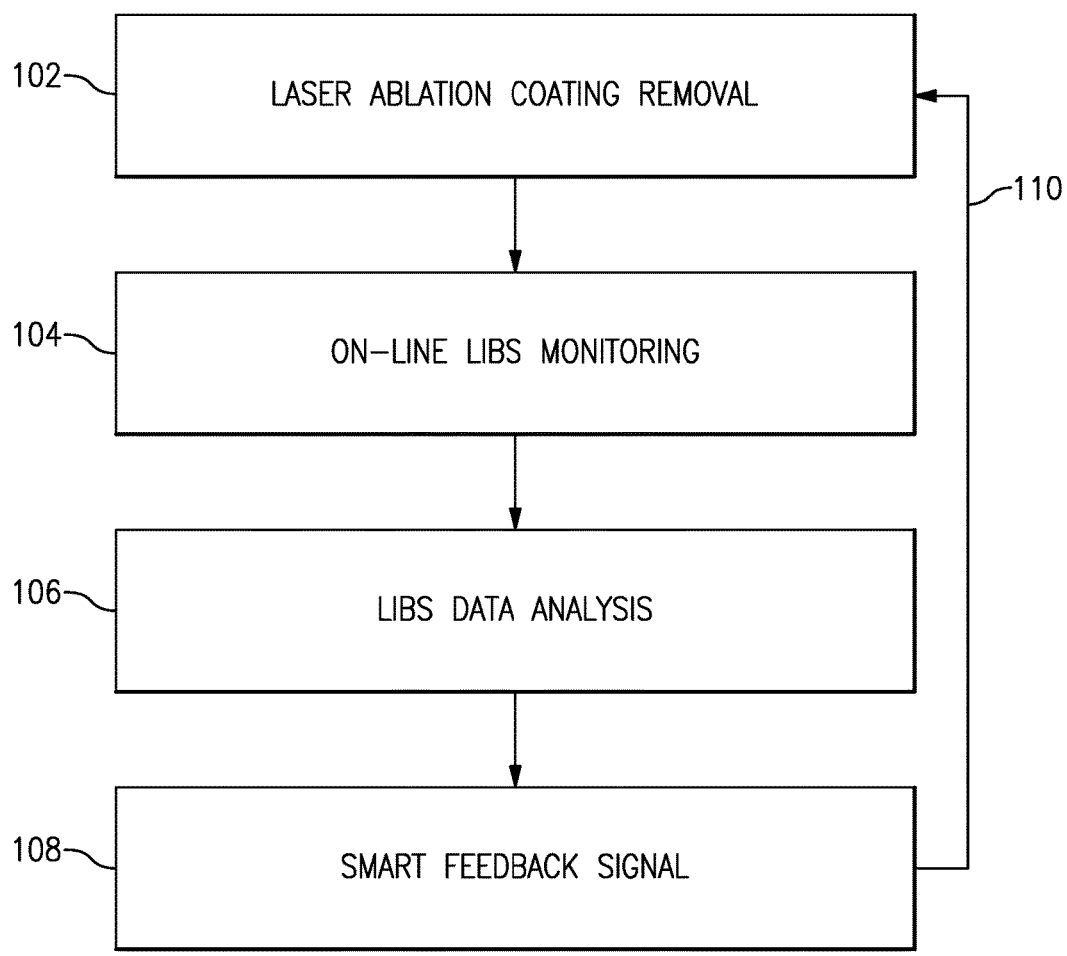

FIG. 4 schematically depicts a LIBS controlled laser ablation system, in accordance with one or more embodiments shown or described herein;

FIG. 5 graphically illustrated reference LIBS spectra from a profile, after preprocessing, in accordance with one or more embodiments shown or described herein; and FIG. 6 is a schematic block diagram of a laser ablation coating removal process using the LIBS controlled laser ablation system of FIG. 4, in accordance with one or more embodiments shown or described herein.

DETAILED DESCRIPTION

The present disclosure will be described in reference to turbine components of a turbomachine, including gas turbines used for power generation and propulsion, though it should be understood that the disclosure can be employed with a variety of components that operate within thermally and chemically hostile environments. More particularly, this disclosure is directed to a system and method that provides real-time compositional feedback to a laser ablation machine in order to identify when the ablation process has reached an optimal end point during a coating removal process. It should be understood that as used herein, the term 'real-time' is intended to mean a time in which input data is processed within seconds so that it is available virtually immediately as feedback. It should additionally be understood that throughout the disclosure the term 'layers' is used to indicate a thickness of a material, although the layers may not have a finite thickness, for example, the transition from one layer to the next may be a steep gradient as opposed to being all one component, followed by a second component in a depth profile.

Figure 1:
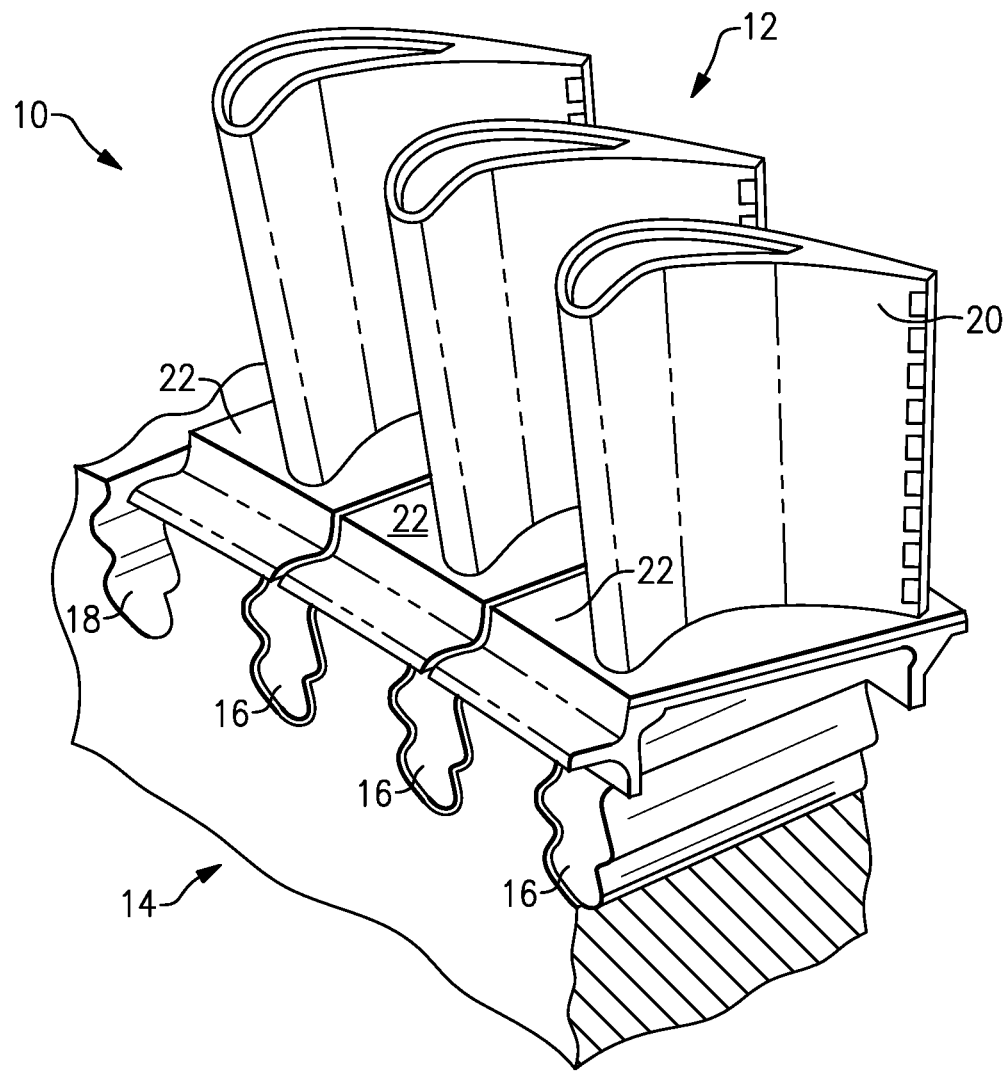
FIG. 1 is a fragmentary perspective view showing an example of a high pressure turbine disk with turbine blades mounted thereto.

For purposes of discussion, a fragment of a high pressure turbine assembly 10 is shown in FIG. 1. The turbine assembly 10 is generally represented as being of a known type, and includes high pressure turbine blades 12 mounted to a disk 14. The blades 12 may be formed of an iron, nickel or cobalt-base superalloy, with nickel-base superalloys typically being preferred. The blades 12 are individually anchored to the turbine disk 14 with dovetails 16 that interlock with dovetail slots 18 formed in the circumference of the disk 14. Each blade 12 has an airfoil 20 and platform 22 against which hot combustion gases are directed during operation of the turbomachine, and whose surfaces are therefore subjected to severe attack by oxidation, hot corrosion and erosion, as well as contamination by particulates. To provide protection to the surface of the blades 12 one or more coating materials may be applied. It is anticipated herein that the coating materials applied to blade 12, may include, but are not limited to, at least one of a thermal barrier coating, a bond coat and an environmental barrier coating.

Of particular interest during the manufacture and/or maintenance of the blade 12 and deposition of a protective coating material thereon, are a plurality of trailing edge cooling slots 24 that may become at least partially covered during the coating process. In this area, tight tolerances necessitate optimized laser ablation to avoid tedious manual inspection and then rework which is time consuming and incurs high manufacturing cost. During fabrication of the blade 12, laser removal may be utilized to remove the protective coating material from the trailing edge slots 24 covered during the coating process, without damaging underlying bond coatings, or the like.

Figure 3:
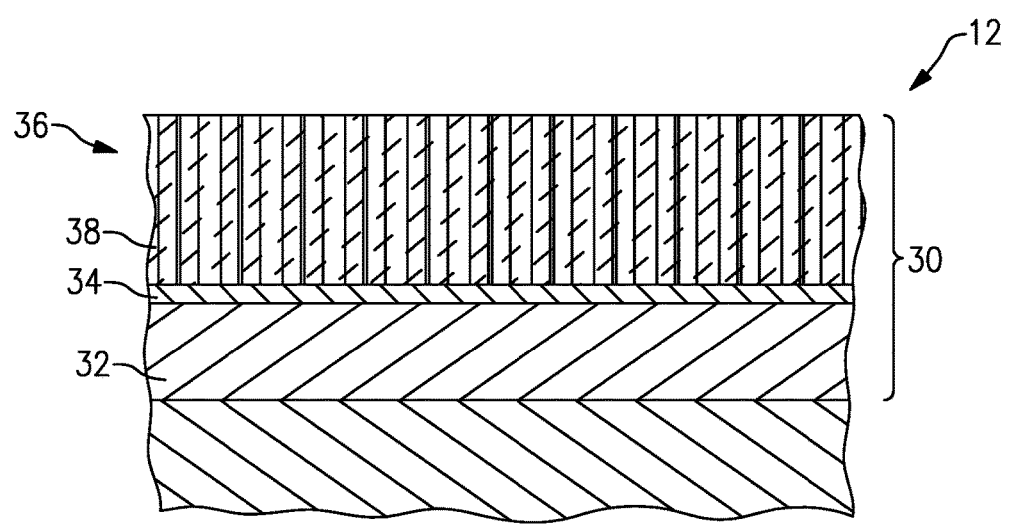
FIG. 3 is a fragmentary cross-sectional view of a thermal barrier coating (TBC) system on an airfoil surface of the blade shown in FIGS. 1 and 2.

Referring more specifically to FIG. 3, in an embodiment the surfaces of the airfoils 12 are protected by one or more protective coating material layers, such as a TBC coating, a bond coating and/or an environmental barrier coating. More particularly, as best illustrated in FIG. 3, in an embodiment the surfaces of the airfoils 12 are protected by a TBC system 30, represented in FIG. 3 as including a metallic bond coat 32 that overlies the surface of the blade 12, and defining a three-dimensional surface. As widely practiced with TBC systems for components of turbomachines, the bond coat 32 may be an aluminum-rich composition, such as an overlay coating of an MCrAlX alloy or a diffusion coating such as a diffusion aluminide or a diffusion platinum aluminide, all of which are well-known in the art. Aluminum-rich bond coats develop an aluminum oxide (alumina) scale 34, which grows as a result of oxidation of the bond coat 32. The alumina scale 34 chemically bonds a TBC 36, formed of a thermal-insulating material, to the bond coat 32. The TBC 36 of FIG. 3 is represented as having a strain-tolerant microstructure of columnar grains 38. As known in the art, such columnar microstructures can be achieved by depositing the TBC 36 using a physical vapor deposition (PVD) technique, such as EBPVD. The disclosure is also applicable to noncolumnar TBC deposited by such methods as plasma spraying, including air plasma spraying (APS). A TBC of this type is in the form of molten "splats," resulting in a microstructure characterized by irregular flattened (and therefore noncolumnar) grains and a degree of inhomogeneity and porosity. As with prior art TBC's, the TBC 36 of this disclosure is intended to be deposited to a thickness that is sufficient to provide the required thermal protection for the blade 12. A typical material for the TBC 36 is an yttria-stabilized zirconia (YSZ), such as a composition containing about 3 to about 8 weight percent yttria (3-8% YSZ), though other ceramic materials could be used, including but not limited to nonstabilized zirconia, or zirconia partially or fully stabilized by magnesia, ceria, scandia or other oxides. In addition, typical material for the bond coat 32 and an included environmental barrier coating may include silicon, ytterbium, platinum and/or aluminium.

In conventional laser ablation processes, the inspection utilized TBC removal, such as proximate the cooling slots 24, is off line and based on optical inspection with no information regarding the chemical profile of the coating. Optimal laser parameters and number of passes needed for complete removal of the coating material are empirically determined by trial and error, resulting in low first time yield. Rework to complete the coating removal is tedious and time consuming. Of particular interest to the present disclosure is the ability to remove the TBC 36 using laser ablation regardless of tight tolerances, variations in the coating thickness and the avoidance of sublayer damage. In many instances the coating thickness has some variation so a correct number of passes cannot be determined without in-line feedback of ablation depth/chemical composition.

Disclosed herein is a system and method for coating removal employing laser induced breakdown spectroscopy, referred to herein as a LIBS controlled laser ablation system 40, as best illustrated in FIG. 4. The system integrates a chemically specific measurement system with the existing laser removal process for in-process monitoring and real-time control during the laser ablation process. The system 40 makes use of laser-induced breakdown spectroscopy (LIBS), also known as laser pulse spectroscopy (LPS) and laser-induced plasma spectroscopy (LIPS). As known in the art, LIBS entails projecting a pulsed laser beam onto a material at a power density sufficient to vaporize (ablate) a small portion of the material and generate a luminous plasma plume that contains the characteristic atomic emission lines of elements within the material, which are then collected for spectral analysis.

In an embodiment, the LIBS controlled laser ablation system 40 includes laser ablation parameters that are empirically set to be conservative. Any residual TBC 36 remaining after laser ablation will be removed during rework. The LIBS controlled laser ablation system 40 enables inline monitoring of the laser ablation process and provides real-time chemical information of the materials removed by the laser which is unique to each coating layer in the TBC system 30. The chemical information obtained by the LIBS controlled laser ablation system 40 is then used as a feedback signal (described presently) to control the laser. This will provide intelligence to stop the laser when the chemical signature obtained by the LIBS controlled laser ablation system 40 indicates a specified layer of the TBC system 30 is completely removed. Additionally, the LIBS information obtained by the LIBS controlled laser ablation system 40 can be used to dynamically optimize the laser parameters during coating removal process. Such optimization of parameters may include adjusting scan speed, scan area, scan volume, pulse overlap, laser pulse frequency, laser pulse width, laser spot size, and/or peak pulse power to achieve the desired tolerances. The LIBS information obtained by the LIBS controlled laser ablation system 40 can also provide both depth and spatial distribution of chemical composition during ablation process.

Referring more specifically to FIG. 4, illustrated is the LIBS controlled laser ablation system 40, including an overview of the complete system, indicated at 42, and the source/collections optics, indicated at 44. The LIBS controlled laser ablation system 40 includes a fiber laser 46, a scan head 48 and a spectrometer 50 optically coupled to one another. In an embodiment, the fiber laser 46 and the scan head 48 are chosen to have similar specifications (laser pulse energy, spot size and frequency) to that of a laser set-up in a known laser ablation machine. During operation of the LIBS controlled laser ablation system 40, a laser beam 52 (i.e., 1064 nm) is launched from the fiber laser 46, expanded and collimated by a beam expander 54 and is then incident on a turning mirror 56. The turning mirror 56 directs the laser light 52 into the scan head 48. In an embodiment, the turning mirror 56 directs the laser light 52 into the scan head 48 with a standard F160 mm F-theta lens. The laser light 52 and the scan head 48 are controlled by a dedicated computer 58 which allows flexibility in the laser power and scan pattern incident on a sample, such as the airfoil 12, in which a coating, such as TBC 36, is to be removed.

In FIG. 4, a laser beam 52 is represented as being projected in pulses onto a TBC-coated surface of a blade 12 (e.g., FIGS. 1 and 2), resulting in vaporization of a small portion of the TBC 36, and generating a luminous plasma plume 62. The LIBS technique then utilizes the characteristic atomic emission lines (characteristic radiation) of elements within the plasma plume 62 to detect and analyze the chemical composition of the material being removed. The utilization of LIBS techniques to analyze the compositions of coatings and coating deposits is disclosed in commonly-assigned U.S. Pat. No. 6,762,836 to Benicewicz et al., U.S. Pat. No. 7,016,035 to Wu et al., and U.S. Pat. No. 7,064,825 to Viertl et al., whose contents relating to the components and operation of LIBS-based systems are incorporated herein by reference.

In an embodiment, the laser beam 52 is projected across a relatively large surface region of the TBC 36. According to another embodiment, the laser beam 52 can be directed at the blades 12 of the turbine assembly 10 for coating removal while the blades 12 remain installed within turbine.

The system 40 is represented in FIG. 4 as generating the pulsed laser beam 52, such as with a Nd:YAG nanosecond laser 53, having a wavelength range from 100 nm-11000 nm, such as 1070 nm. The nanosecond laser 53 generates very low peak power in comparison to femtosecond lasers. The laser 53 generates energy in the near infrared region of the electromagnetic spectrum. It is foreseeable that other laser generators could be employed, for example, of the Excimer (Excited dimer) type that generates energy in the visible and ultraviolet regions. As is typical in LIBS systems, the laser 53 is operated to generate the laser beam 52 at its fundamental wavelength or any of its harmonic wavelengths, or otherwise any low peak power pulsed laser capable of generating sufficiently focused intensities to vaporize and form a luminous plasma of the targeted material, which in this case is the TBC 36 on the surface of the airfoil 12. As such, the primary elements to be detected are those contained within the TBC 36. Suitable laser beam power densities for this purpose are believed to be about 0.1 $GW/cm^2$ During the process of coating removal from the blade 12, the laser beam 52 is pulsed to ablate a very small amount of coating material, such as TBC 3, which generates the plasma plume 62 on the surface of the airfoil 12. The plasma plume 62 produces an atomic emission spectrum that is representative of the chemical makeup of the coating material being removed. With each pulse of the laser light 52, plasma light 66 is generated and a small amount of the coating material, and more particularly TBC 36, at the surface of the airfoil 12 is removed. Delayed spectroscopic measurements of the plasma plume 62 are used to detect and measure the various specific transient species within the plasma. In an embodiment, the collected light may be in the range from 100 nm-1000 nm covering the visible range of the electromagnetic spectrum.

Depth profiling to determine to what depth the coating material has been removed, can be achieved by collecting a LIBS signal 68 generated by a spectrometer 70 over multiple sequential laser light 52 pulses. In this way, the LIBS controlled laser ablation system 40 has the potential to achieve layer-to-layer chemical contrast in the laser ablation coating removal process. The LIBS signal 68 is employed to provide chemical resolution as a feedback signal 72 to control and optimize the laser ablation process in real-time. The LIBS signal 68 is used to determine when the removal of a desired coating material layer is complete without breaking into the sublayers. To accomplish such, the LIBS controlled laser ablation system 40 includes a feedback algorithm 80 configured to act on the obtained LIBS signal 68 directly and does not rely on a database for which to compare the sampled LIBS spectrum. In response, the system 40 provides via the feedback signal 72 control and optimization of multiple parameters including scan speed, scan area, scan volume, pulse overlap, laser pulse frequency, laser pulse width, laser spot size, and/or peak pulse power to achieve the desired tolerances. The disclosed system 40 is able to control multiple parameters to adapt to the part topography as opposed to just increasing and decreasing laser power.

During operation the laser beam 52 is preferably pulsed, such that multiple measurements are performed, with each measurement following a laser pulse. With knowledge of the original elements in the TBC 36 (such as zirconium, yttrium, and oxygen if formed of YSZ), the elements in the plasma plume 62 can be detected and their amounts quantitatively determined by measuring the intensity of their characteristic atomic emission lines (characteristic radiation) emitted from the plasma. Detection and spectral analysis are performed by collecting the characteristic radiation emanating from the plasma with the collection optics 44, conducting the characteristic radiation back through the collection optics 44, which directs the radiation to the high-speed digital spectrometer 70. In an embodiment, the spectrometer 70 spectrally disperses and focuses the radiation onto a detector 74, for example an intensified charge-coupled device (ICCD), or another suitable array detector, for example, a photo-diode array (PDA). A control unit 76, such as a computer, can then be employed to display, store, and manipulate the spectral data obtained from the detector 74. The control unit 76 is preferably capable of analyzing the emission spectra from multiple plasma events in real-time and display or save the data for future evaluation. Various commercial software packages for performing these operations are known and available for programming the control unit 76, and will not be discussed in any detail here.

In the illustrated embodiment of the LIBS controlled laser ablation system 40, the collection optics 44 employ an off-axis telephoto lens pair 78 to collect the plasma light 66 generated by each pulse of the laser beam 52. The collected plasma light 66 is launched into a core optical fiber 57 and then relayed to the spectrometer 70. In an embodiment, the spectrometer 70 is set-up to collect 10 spectra per second. Acquisition time and number of pulses of the laser beam 52 collected may vary depending on chosen design parameters.

By employing LIBS technology for chemical resolution in the feedback signal 72, real-time control and optimization of the laser ablation process using the LIBS controlled laser ablation system 40 may be possible. The LIBS controlled laser ablation system 40 provides the potential to determine when the removal of a desired layer, such as TBC 36, is complete and stop the ablation process to prevent breaking into and/or damaging the sublayers, such as a bond coat layer, based on the real-time LIBS signal 68.

Implementation of the system 40 involves measuring and comparing the intensities of the unique wavelengths of the elemental constituents of the TBC 36, namely, zirconium, yttrium, and oxygen. As such, the spectrometer 70 preferably has a spectral range for selectively tracking at least three elements, though the tracking of a fewer or a greater number of elements is foreseeable. In addition, spectral tracking of alternate elements may be provided, such as silicon, ytterbium, platinum and aluminium, such as may typically be found in the bond coat layer 82 and/or environmental barrier coating. With proper correction for the natural differences in excitation efficacy, the ratio of the corrected intensities provides the ratio of these and other elements vaporized by the laser beam 52, enabling the detection of elements present in sub-layers to be ascertained, when the laser ablation depth has exceeded the thickness of the TBC 36.

Figure 2:
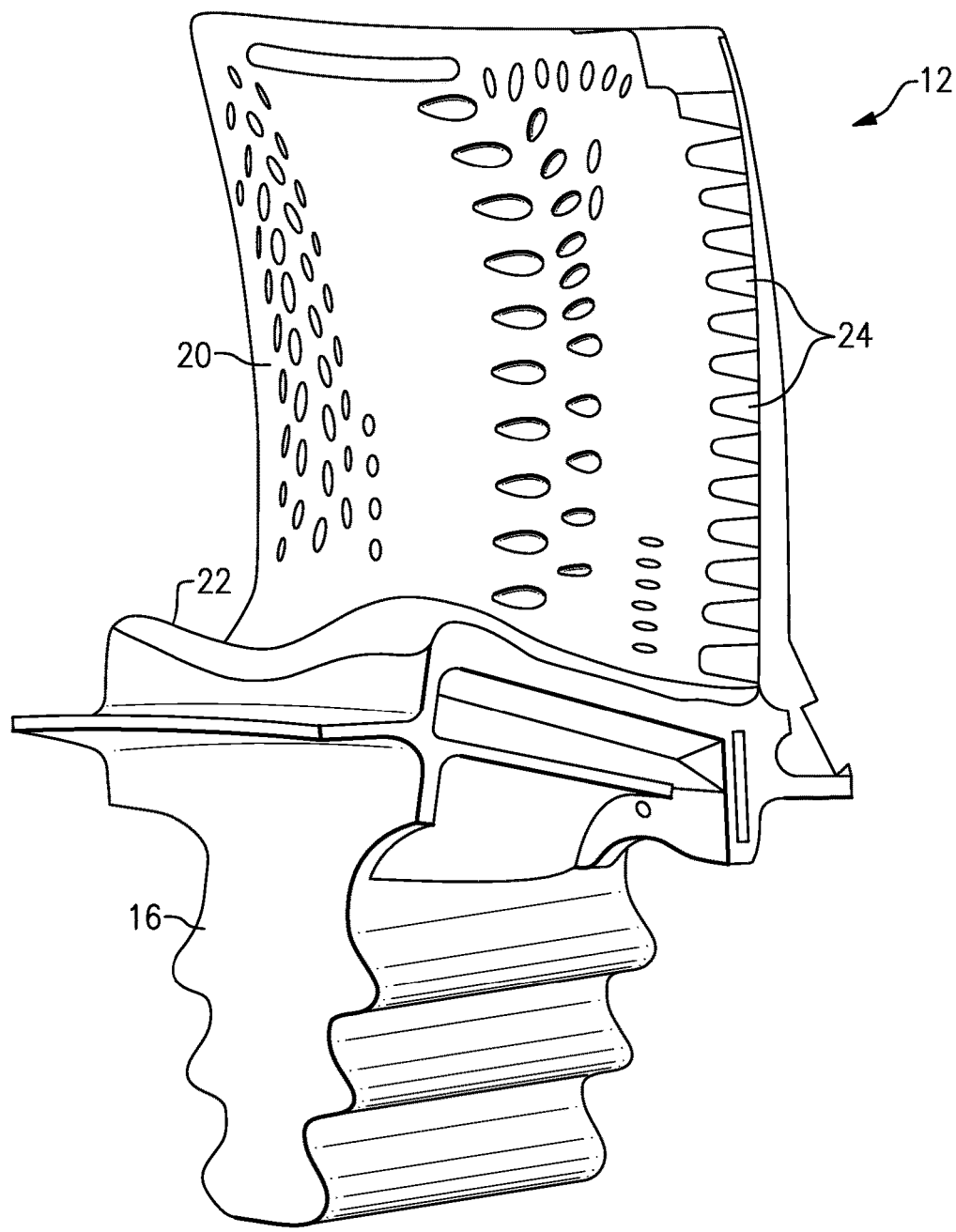
FIG. 2 is a fragmentary perspective view of a turbine blade of FIG. 1, in accordance with one or more embodiments shown or described herein.

As disclosed herein the LIBS controlled laser ablation system 40 utilizes an adaptive laser scanning approach for targeted coating/material removal. As illustrated in FIGS. 1 and 2, the airfoil 12 has a three-dimensional aspect that is important for their function and thus the topography of the region of interest is of concern during the ablation process. Accordingly, referring again to FIG. 4, the control unit 76 includes a topography map that provides initial parameters for the coating removal process. More specifically, as part of the feedback control, a topography map of the sample (i.e. a CAD file, structured light image, photograph etc.) is part of an operational algorithm where regions of interest are identified for the coating removal. The LIBS controlled laser ablation system 40 uses the LIBS signal 68 to adaptively ablate the three-dimensional surface (turbine blade 12) that has a residual or undesired coating, such as TBC 36 thereon. The LIBS controlled laser ablation system 40 enables control of the laser ablation result in three-dimension: depth (Z) and surface (X and Y). In lieu of using an XYZ motion stage, a high speed galvanometer mirror (not shown) within the scan head 48 scans the laser beam 52 across the region of interest with very uniform pulse-to-pulse overlap, thereby generating a very precise depth control within a very small area with complex shapes. In an embodiment, the scan head 48 may comprise multiple high speed galvanometer mirrors where each is able to pivot at a fast rate to translate a laser beam along a single axis, one mirror for the x-axis and one for the y-axis. An XYZ motion stage would not move sufficiently fast for the small feature area of interest, and would end up with deeper cut/hot spot.

Referring now to FIG. 5, illustrated in graph 80 are reference LIBS spectra from a profile, after preprocessing. More particularly, illustrated on axis 82 are the wavelengths of a TBC layer, generally referenced 84, a bond coat layer, generally referenced 86 and a super alloy layer, generally referenced 88, as a function of normalized intensity, plotted on axis 90. As illustrated, in the 200 nm-400 nm spectral region there are several non-overlapping atomic emission lines. The intensity of these lines can be used to differentiate signal arising from the TBC layer (such as TBC 36 of FIG. 3) vs. a signal arising from the BC layer (such as underlying bond coat layer 32 of FIG. 3). By plotting these intensities as a function of depth, layer dependent depth profile plots are generated. For this spectral region, the signal arising from an underlying super alloy layer has low signal to noise ratio. Signals from the super alloy layer could be improved by looking at a different or expanded spectral region or perhaps by improving the collection optics. In the embodiment disclosed herein, however, the illustrated spectral of FIG. 5 is sufficient for detecting the transition from the TBC layer 36 to the bond coat layer 32, as there are a number of non-overlapping atomic emission lines that can be used for chemical contrast.

During LIBs processing, after preprocessing, the spectrum is reduced to 3 numbers to represent each of the three layers (TBC, BC, SA). This is accomplished by combining the intensity values from several of the atomic emission lines corresponding with each layer and then calculating the median intensity value. These numbers are then plotted as a function of the acquisition sequence to obtain a depth profile. Comparative thresholding can then be used to determine layer transitions.

This same approach could also be accomplished with a univariate method where a single atomic emission line for each layer of interest would be used to visualize the transition between layers or with a multivariate method where contributions from each atomic emission line would be used to optimize the signal to noise in deciphering layer-to-layer signal. The approach, described with respect to FIG. 5, gains signal to noise over the true univariate method by using multiple spectral bands, but can still be operated on a single spectrum. In contrast, the multivariate approach would need a representative basis-set to build a multivariate model; once a multivariate model is made, then layer-to-layer transition predictions can be made.

Referring now to FIG. 6, illustrated is a schematic block diagram of a laser ablation coating removal process 100 using the LIBS controlled laser ablation system 40 of FIG. 4, in accordance with one or more embodiments shown or described herein. More specifically, illustrated is a step 102 in which standard laser ablation coating removal is utilized. During this step, a pulsed laser beam is projected onto a material at a power density sufficient to vaporize (ablate) a small portion of the material and generate a luminous plasma plume that contains characteristic atomic emission lines of elements within the material. At step 104, on-line LIBS monitoring takes place, whereby multiple optical collection devices and a LIBS spectrometer are used to obtain data over multiple sequential laser light pulses and generate a LIBS signal. In an embodiment, the LIBS signal is collected in way that enables chemical mapping with spatial resolution down to sub-micron range. Next in a step 106, the LIBS data is analyzed. More particularly, the LIBS data is analyzed, by one or more of a univariate and multivariate approach, using fast data processing to provide real-time chemical composition of the ablated material. The obtained data will indicate the progress of the laser ablation coating removal process. In a subsequent step 108, a smart feedback signal related to the composition information is generated to provide ongoing, real-time control, of the laser and optimization of multiple processing parameters, including, but not limited to, adjusting scan speed, scan area, scan volume, pulse overlap, laser pulse frequency, laser pulse width, laser spot size, and/or peak pulse power to achieve the desired tolerances, via step 110.

In view of the above, it can be appreciated that the system 40 can be used to provide controlled laser ablation of a coating material, such as TBC 36, on the turbine blades 12 (as well as other hot gas path components of the turbine), without limitation to regular maintenance schedules and without relying simply on visual observations to determine the depth and/or completeness of the laser ablation. Instead, the system 40 provides for real-time monitoring and control of the laser ablation process, and adaptive optimization of multiple parameters including adjusting scan speed, scan area, scan volume, pulse overlap, laser pulse frequency, laser pulse width, laser spot size, and/or peak pulse power to achieve the desired tolerances. LIBS signals are used to monitor and control the laser ablation TBC coating removal in real-time.

Advantageously, the system 40 can typically perform the desired analysis using a series of small pulses, with the amount of material removed being adjustable by the intensity and number of laser pulses used at any given location. Accordingly, the LIBS controlled laser ablation system 40, as disclosed herein, enables the use of obtained LIBS signals to be used to monitor and control the laser ablation removal of a coating material, such as a TBC coating, in real-time. Consequently, notable potential advantages of this disclosure can include a system that is highly flexible and capable of monitoring most elements in the periodical table, thus can be used to control laser ablation of a variety of coating materials, i.e. it can be used for both new make and coating repair. Additional potential advantages include a system that is forgiving to changes up-stream of the ablation process, i.e. if a layer thickness changes the system would easily adapt to that change and still provide the necessary feed-back to control the ablation process. In addition, known laser ablation system do not need to change. The LIBS system may be provided as an add-on to monitor a signal that is already generated by the ablation process. Thus the system is technically relatively simple to implement and demonstrate with existing equipment While the disclosure has been described in terms of particular embodiments, it is apparent that other forms could be adopted by one skilled in the art. For example, it is foreseeable that functionally-equivalent devices and equipment could be used in place of the devices and equipment noted and described in reference to the disclosed embodiments. Furthermore, the disclosed disclosure is not limited to laser ablation on turbomachine components, but could find application in other circumstances where spectral analysis of a material during laser ablation is desired. Accordingly, the scope of the disclosure is to be limited only by the following claims.

While there have been described herein what are considered to be preferred and exemplary embodiments of the present disclosure, other modifications shall be apparent to those skilled in the art from the teachings herein, and it is, therefore, desired to be secured in the appended claims all such modifications as fall within the true spirit and scope of the disclosure.

The invention claimed is:

1. A system for performing laser induced breakdown spectroscopy during a laser ablation coating removal process, the system comprising:
   a laser energy source configured to perform the laser induced breakdown spectroscopy and laser ablation coating removal process;
   a scan head interconnected with the laser energy source to receive a laser beam emitted therefrom, the scan head positioned sufficiently close to an article having a three-dimensional surface to enable the laser beam exiting the laser energy source to be directed onto the three-dimensional surface of the article defined by a coating to ablate at least a portion of the coating;
   one or more collection optics to collect radiation emitted from a laser-induced plasma generated by the laser beam at the three-dimensional surface of the coating;
   means for spectrally analyzing the radiation collected by the collection optics and generate a signal representative of the chemical composition of the collected radiation; and
   a control unit to receive the signal from the means for spectrally analyzing the radiation and generate a feedback signal for control and optimization of one or more operational parameters of the laser energy source to adapt to a topography of the three-dimensional surface in real-time,
   wherein the control unit comprises a topography map of the article as part of a feedback algorithm.

2. The system according to claim 1, wherein the one or more operational parameters include a scan speed, a scan area, a scan volume, a laser pulse overlap, a laser pulse frequency, a laser pulse width, a laser spot size and a peak pulse power to achieve desired tolerances.

3. The system according to claim 1, wherein the feedback algorithm is configured to act on the signal generated by the means for spectrally analyzing the radiation to control and optimize the one or more operational parameters of the laser energy source in real-time.

4. The system according to claim 1, wherein the laser energy source is a nanosecond laser.

5. The system according to claim 1, wherein the means for spectrally analyzing the radiation collected by the collection optics is a high-speed digital spectrometer.

6. The system according to claim 1, wherein the laser energy source and the collection optics are cooperatively adapted to vaporize the coating and collect at least a portion of the radiation emitted from a laser-induced plasma, and the spectral analyzing means is adapted to selectively detect and chemically analyze the radiation emitted from the laser-induced plasma.

7. The system according to claim 1, wherein the coating is at least one of a thermal barrier coating, a bond coat, and an environmental barrier coating.

8. The system according to claim 7, wherein the thermal barrier coating contains one or more of zirconium, yttrium or oxygen and wherein the bond coating and the environmental harrier coating contain one or more of silicon, ytterbium, platinum and aluminum.

9. The system according to claim 8, wherein the means for spectrally analyzing the radiation includes a spectral range for selectively tracking at least two elements.

10. A system for laser induced breakdown spectroscopy of a three-dimensional surface of a turbine component of a turbomachine during a laser ablation coating removal process, the system comprising:
    a laser energy source configured to perform the laser induced breakdown spectroscopy and the laser ablation coating removal process;
    a scan head interconnected with the laser energy source to receive a laser beam emitted therefrom, the scan head positioned sufficiently close to the turbine component to enable the laser beam exiting the laser energy source to be directed onto the three-dimensional surface of the turbine component defined by a coating, to ablate at least a portion of the coating;
    one or more collection optics to collect radiation emitted from a laser-induced plasma generated by the laser beam at the three-dimensional surface of the turbine component;
    a spectrometer to spectrally analyze the radiation collected by the collection optics and generate a signal representative of the chemical composition of the collected radiation; and
    a control unit to receive the signal from the spectrometer and generate a feedback signal for control and optimization of one or more operational parameters of the laser energy source in real-time to adapt to a topography of the three-dimensional surface in real-time,
    wherein the control unit comprises a topography map of the article as part of a feedback algorithm.

11. The system according to claim 10, wherein the one or more operational parameters include a scan speed, a scan area, a scan volume, a laser pulse overlap, a laser pulse frequency, a laser pulse width, a laser spot size and a peak pulse power to achieve desired tolerances.

12. The system according to claim 10, wherein the feedback algorithm is configured to directly act on the signal generated by the spectrometer to control and optimize the one or more operational parameters of the laser energy source in real-time.

13. The system according to claim 10, wherein the laser energy source is a nanosecond laser.

14. The system according to claim 10, wherein the coating is a thermal barrier coating, the laser energy source and the collection optics are cooperatively adapted to vaporize the thermal barrier coating and collect at least a portion of the vaporized thermal barrier coating, and the spectrometer is adapted to selectively detect and chemically analyze the vaporized portion of the thermal barrier coating.

15. The system according to claim 14, wherein the thermal barrier coating contains one or more of zirconium, yttrium or oxygen.

* * * * *